United States Patent
Courtney et al.

(10) Patent No.: US 9,320,548 B2
(45) Date of Patent: Apr. 26, 2016

(54) SPINAL CROSS-CONNECTOR AND METHOD FOR USE OF SAME

(71) Applicant: Eminent Spine LLC, Georgetown, TX (US)

(72) Inventors: Steve Courtney, Plano, TX (US); David Freehill, Temple, TX (US)

(73) Assignee: Eminent Spine LLC, Georgetown, TX (US)

( * ) Notice: Subject to any disclaimer, the term of this patent is extended or adjusted under 35 U.S.C. 154(b) by 0 days.

(21) Appl. No.: 13/915,451

(22) Filed: Jun. 11, 2013

(65) Prior Publication Data

US 2013/0274802 A1 Oct. 17, 2013

Related U.S. Application Data

(63) Continuation of application No. 12/630,817, filed on Dec. 3, 2009, now Pat. No. 8,460,342.

(60) Provisional application No. 61/119,616, filed on Dec. 3, 2008.

(51) Int. Cl.
 *A61B 17/70* (2006.01)

(52) U.S. Cl.
 CPC .................. *A61B 17/7052* (2013.01)

(58) Field of Classification Search
 CPC .................. A61B 17/7049; A61B 17/7052
 USPC ......... 606/246, 250, 251, 252, 253, 256, 258, 606/259, 260, 264, 276, 277, 278; 403/362; 411/393
 See application file for complete search history.

(56) References Cited

U.S. PATENT DOCUMENTS

| | | | |
|---|---|---|---|
| 4,611,582 A | 9/1986 | Duff | |
| 5,702,393 A | 12/1997 | Pfaifer | |
| 5,980,523 A | 11/1999 | Jackson | |
| 6,217,578 B1 | 4/2001 | Crozet et al. | |
| 6,261,288 B1 | 7/2001 | Jackson | |
| 6,302,882 B1 * | 10/2001 | Lin et al. | 606/252 |
| 6,368,320 B1 | 4/2002 | Le Couedic et al. | |
| 6,402,751 B1 * | 6/2002 | Hoeck et al. | 606/252 |
| 6,416,515 B1 | 7/2002 | Wagner | |
| 6,702,814 B2 | 3/2004 | Walulik et al. | |

(Continued)

OTHER PUBLICATIONS

ISR, PCT/US2009/066662, Steve Courtney, Jan. 29, 2010.

*Primary Examiner* — Pedro Philogene
*Assistant Examiner* — David C Comstock
(74) *Attorney, Agent, or Firm* — Scott T. Griggs; Griggs Bergen LLP

(57) ABSTRACT

A spinal cross-connector for connection between adjacent first and second rods and method for use of the same are disclosed. In one embodiment, a coupling member including a bar extends from a body portion opposite to and in longitudinal axial alignment with a c-shaped arm. A second coupling member which includes a rack extends from a body portion opposite to and in longitudinal axial alignment with a another c-shaped arm. The rack is superposed in a selectively adjustable overlapping mechanical engagement with the bearing surface. Each c-shaped arm includes an arcuate extension extending substantially parallel to the bar to define a gripping pocket. A set screw includes a conical profile that extends substantially perpendicular to the arcuate extension. The advance of the set screw is operable to urge the rod into pressing contact with the gripping pocket to secure the rod therein.

4 Claims, 4 Drawing Sheets

(56) References Cited

U.S. PATENT DOCUMENTS

| | | |
|---|---|---|
| 6,752,807 B2 | 6/2004 | Lin et al. |
| 6,875,211 B2 | 4/2005 | Nichols et al. |
| 7,066,938 B2 | 6/2006 | Slivka et al. |
| 2005/0228375 A1 | 10/2005 | Mazda et al. |
| 2005/0228377 A1 | 10/2005 | Chao et al. |
| 2006/0036240 A1 | 2/2006 | Colleran et al. |
| 2006/0064093 A1 | 3/2006 | Thramann et al. |
| 2006/0122597 A1 | 6/2006 | Jones et al. |
| 2006/0247637 A1 | 11/2006 | Colleran et al. |
| 2006/0271045 A1 | 11/2006 | Hubbard et al. |
| 2006/0282078 A1 | 12/2006 | Labrom et al. |
| 2007/0016197 A1 | 1/2007 | Woods et al. |
| 2007/0083201 A1 | 4/2007 | Jones et al. |
| 2007/0219556 A1 | 9/2007 | Altarac et al. |
| 2008/0097440 A1 | 4/2008 | Reiley et al. |

* cited by examiner

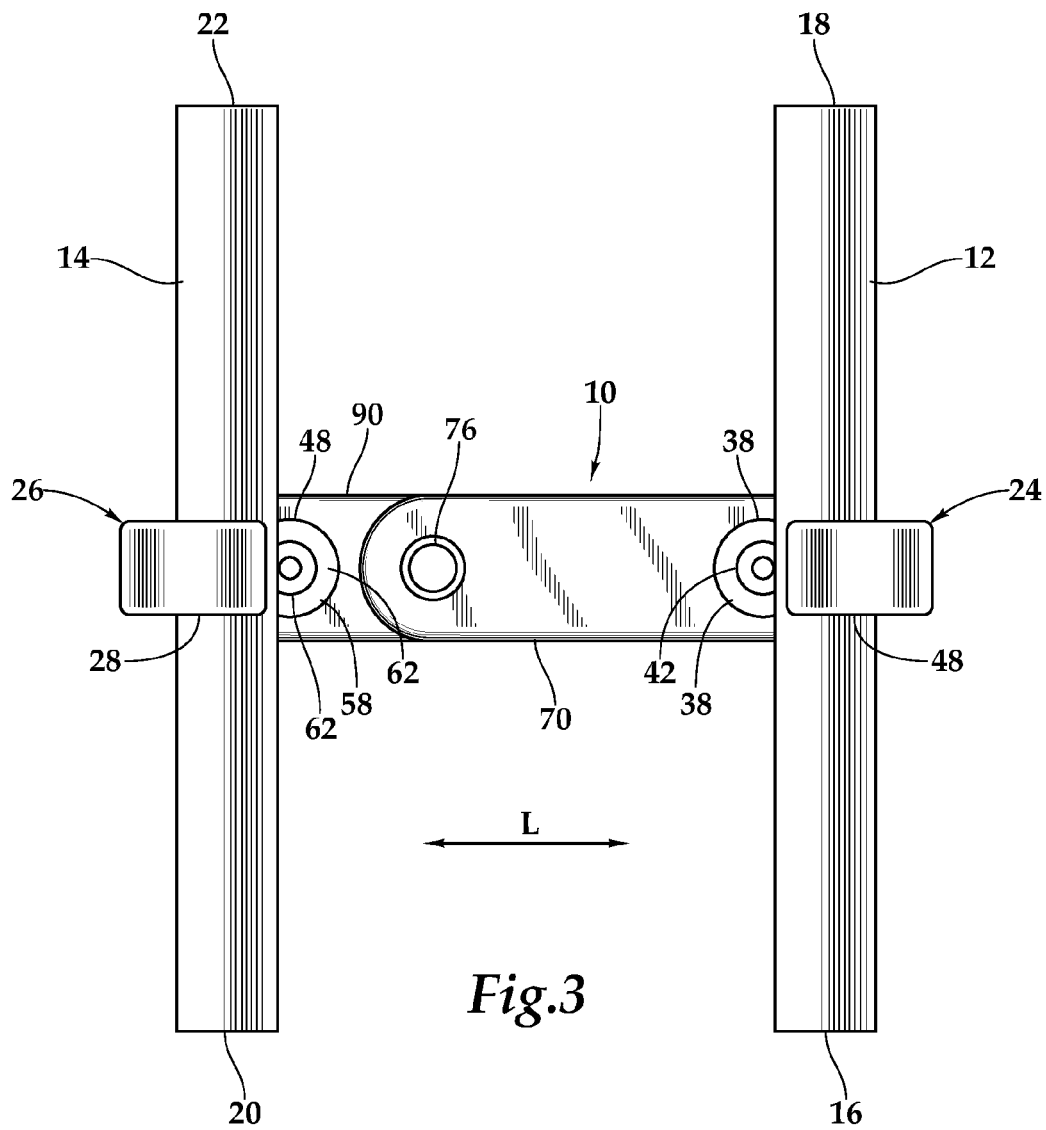
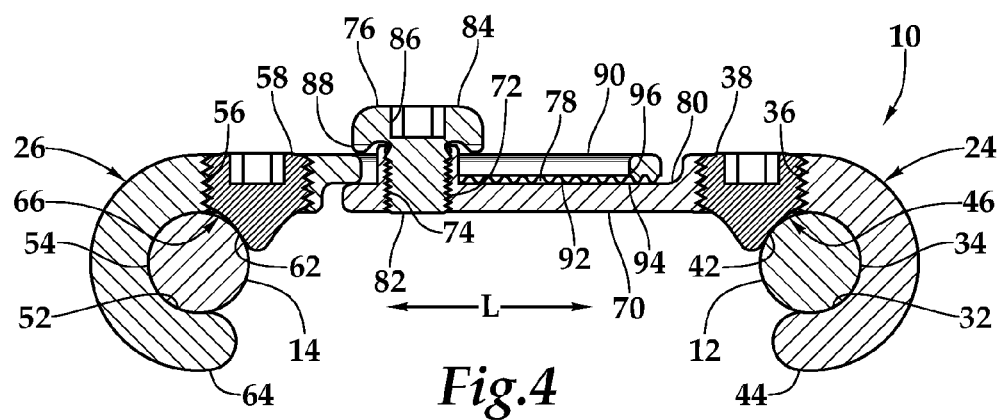

SPINAL CROSS-CONNECTOR AND METHOD FOR USE OF SAME

PRIORITY STATEMENT & CROSS-REFERENCE TO RELATED APPLICATIONS

This application is a continuation of patent application Ser. No. 12/630,817 entitled "Spinal Cross-connector and Method for Use of Same," filed on Dec. 3, 2009, and issued on Jun. 11, 2013 as U.S. Pat. No. 8,460,342 in the names of Steve Courtney and David Freehill; which claims priority from Ser. No. 61/119,616 entitled "Spinal Cross-connector and Method for Use of Same" and filed on Dec. 3, 2008 in the names of Steve Courtney and David Freehill; which is hereby incorporated by reference for all purposes.

TECHNICAL FIELD OF THE INVENTION

This invention relates, in general, to medical implants useful for orthopedic surgeries and, in particular, to a spinal cross-connecter and method for use of same that provide for the stabilization of posterior elements of the spine and substantially controlling or providing resistance to movement including torque and rotation.

BACKGROUND OF THE INVENTION

Spinal fixation systems are employed in orthopedic surgery to stabilize parts of the spine with the use of longitudinal or orthopedic rods. Typically, a pair of orthopedic rods is affixed to the spine by fasteners such as pedicle screws, which act as anchoring devices, to immobilize the spine and facilitate fusion by holding the vertebrae in a desired spacial relationship for a desired period of time. It has been found that when a pair of parallel orthopedic rods are fastened on respective sides of the spinous process, the spinal fixation system may be strengthened by using a cross-connector to transversely bridge the longitudinal rods together. Depending on the size of the fixation, one or more cross-connectors may be utilized. Each cross-connector or cross-link member includes a pair of opposing coupling members linked together by a transverse bridge member, which may be adjustable or telescoping to vary with an individual's anatomy and the distance between the orthopedic rods. Each of the opposing coupling members is secured to one of the orthopedic rods. Once installed, the spinal cross-connector protects against torsion forces and movement.

Current spinal cross-connectors although effective are not without deficiencies and limitations. Spinal cross-connectors are often utilized at the tail end of a lengthy and tedious orthopedic surgery. It is therefore desirable to have spinal cross-connectors that mount to the orthopedic rods effectively to maintain fixation. It is also desirable to have spinal cross-connectors having a minimum number of mechanical parts requiring a minimum number of mechanical actions to achieve placement and fixation. Existing spinal cross-connectors often include complex clamping arrangements for gripping the orthopedic rods as well as complex telescoping assemblies for bridging the span between the pair of orthopedic rods. Accordingly, a need continues to exist for an improved spinal cross-connector that mates with orthopedic rods and spans the space therebetween with a minimized number of mechanical parts and required mechanical actions.

SUMMARY OF THE INVENTION

A spinal cross-connector for connection between adjacent first and second rods and method for use of the same are disclosed. In one embodiment, a coupling member including a bar extends from a body portion opposite to and in longitudinal axial alignment with a c-shaped arm. A second coupling member which includes a rack extends from a body portion opposite to and in longitudinal axial alignment with another c-shaped arm. The rack is superposed in a selectively adjustable overlapping mechanical engagement with the bearing surface. Each c-shaped arm includes an arcuate extension extending substantially parallel to the bar to define a gripping pocket. A set screw includes a curved or conical profile that extends substantially perpendicular to the arcuate extension. The advance of the set screw is operable to urge the rod into pressing contact with the gripping pocket to secure the rod therein.

In one embodiment of a method for establishing a cross-connection between adjacent first and second rods, a spinal cross-connector is provided. The length of the spinal cross-connector is established by fixing the selectively adjustable overlapping mechanical engagement between the rack and the bar. This step may include advancing a fastener through the rack and the bar to provide a compression fit therebetween. Each rod may be positioned within a gripping pocket defined by an arcuate extension of the first c-shaped arm. Set screws may then be selectively advanced through the respective body portions to urge the rods into engagement with the respective gripping pockets.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 3 is a bottom plan view of the spinal cross-connector of FIG. 1;

FIG. 4 is a side-cross sectional view of the spinal cross-connector of FIG. 1 in an operational embodiment being secured to rods;

DETAILED DESCRIPTION OF THE INVENTION

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention, and do not delimit the scope of the present invention.

Figure 1:
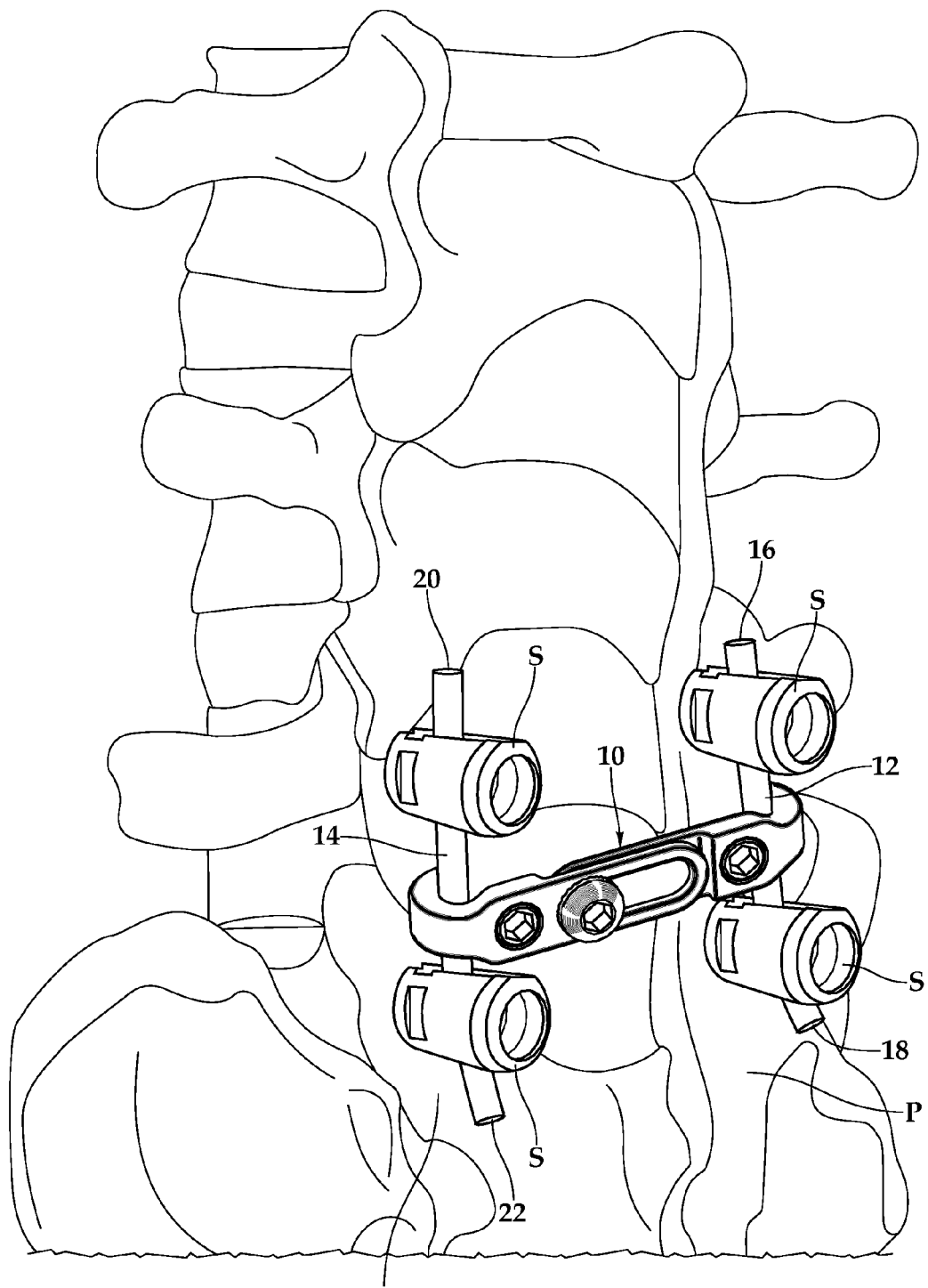
FIG. 1 is an illustrated view of one embodiment of a spinal cross-connector implanted into a human vertebral column.

Referring initially to FIG. 1, therein is depicted one embodiment of a spinal cross-connector 10, implanted into a humane vertebral column. A vertebral pedicle is a dense stem-like structure that projects from the posterior of a vertebra. There are two pedicles per vertebra that connect to other structures such as lamina and vertebral arches. By way of example, the spinal cross-connector 10 may be utilized with a pedicle screw fixation system to correct deformity, treat trauma, or a combination thereof. Additionally, such a spinal cross-connector may be used in instrumentation processes to affix rods to the spine and to immobilize part of the spine to assist fusion by holding bony structures together.

Tulips and pedicles screws, individually and collectively S, are placed down the small bony tube created by the pedicle, which is represented by the letter P, on each side of the vertebra, between the nerve roots. The pedicle screws S grab into the bone of the vertebral body, furnishing a solid hold in the vertebra. That is, in use, four anchoring devices, e.g., tulips, S receive and hold the orthopedic rods 12, 14 at two or more connective spine segments, such as lumbar segments 5 and 6, respectively proximate to rod ends 16, 18, 20, 22. The spinal cross-connector 10 spans the space between the orthopedic rods 12, 14 and interconnects the orthopedic rods 12, 14 to provide an allowance or space for spinal extensor muscles once, for example, the spinal process has been removed.

Figure 2:
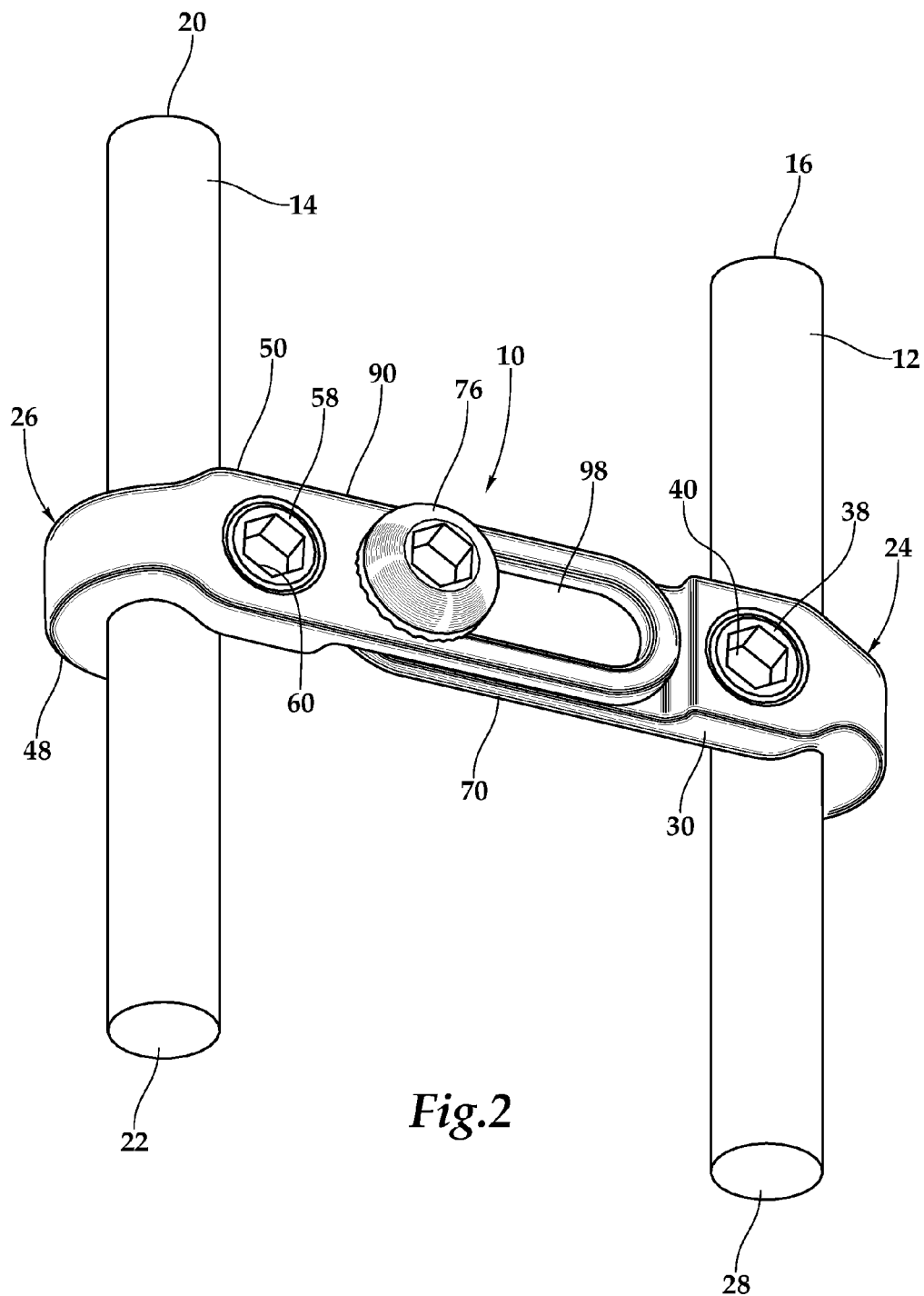
FIG. 2 is a top perspective view of the spinal cross-connector of FIG. 1.

Referring to FIG. 2 through FIG. 4, the spinal cross-connector 10 includes two coupling members 24, 26 bridging the span between the orthopedic rods 10, 12 at a substantially orthogonal position or compensated position therebetween. With respect to the coupling member 24, a c-shaped arm 28 extends from a body portion 30. A gripping pocket 32 located on an interior surface 34 of the c-shaped arm 28 is adapted to accept the orthopedic rod 12 and seat the orthopedic rod 10 therein. A threaded bore 36 is disposed in the body portion 30 for receiving a set screw 38 having a socket 40. With respect to the set screw 38, a curved or conical profile 42 is furnished which complements and substantially continues the interior surface 34 of the gripping pocket 32. The conical profile 42 of the set screw 38 extends substantially perpendicular to an arcuate extension 42 of the c-shaped arm 28, wherein the arcuate extension 42 extends substantially parallel to a flat bar 70 of the body portion 30. In this manner, the conical profile 42 of the set screw 38 and the interior surface 34 define a rod receiving space 44. As illustrated, the opposing coupling member 26 includes similar components; namely, a c-shaped arm 48, a body portion 50, a gripping pocket 52, an interior surface 54, a threaded bore 56, and a set screw 58, a socket 60, a conical profile 62, an arcuate extension 64, and a rod receiving space 66. As shown, in one embodiment, the c-shaped arms 28, 48 define respective gripping pockets 32, 52 that face each other and toward the medial line of the spinal cross-connector 10.

The coupling member 24 includes the aforementioned bar or flat bar 70 extending from the body portion 30 opposite to and in longitudinal axial alignment with the c-shaped arm 28. The flat bar 70 includes an aperture 72 for housing a threaded lug 74 that receives a threaded bolt 76. In another embodiment, the aperture 72 may include a threaded inner diameter instead of the threaded lug, for example. It should be appreciated, that the aperture 72, threaded lug 74, and the threaded bolt 76 may be any type of selectively adjustable fastening member. A bearing surface 78 extends the length of the flat bar 70 from a location proximate to the aperture 72 to an end 80. The threaded bolt 76 includes a body 82 having integral therewith a head 84 and a socket 86 as well as a shoulder 88.

On the other hand, coupling member 26 includes a rack 90, which has teeth 92, extending from the body portion 50 opposite to and in axial alignment with the c-shaped arm 48. The rack 90 includes a slot 98 for receiving the threaded bolt 76 that permits the threaded bolt 76 to be placed therethrough for engagement and then tightening with the threaded lug 74 of the aperture 72. The threaded bolt 76 thereby slidably mates the rack 90 to the flat bar 70. In one embodiment, the flat bar 70 includes a contact surface 94 and the rack 90 includes a contact surface 96 that form a mechanical inter-connection engagement therebetween due to the profile of the contact surface 94 and/or contact surface 96. This mechanical interconnection engagement may provide a friction fit therebetween.

Figure 5:
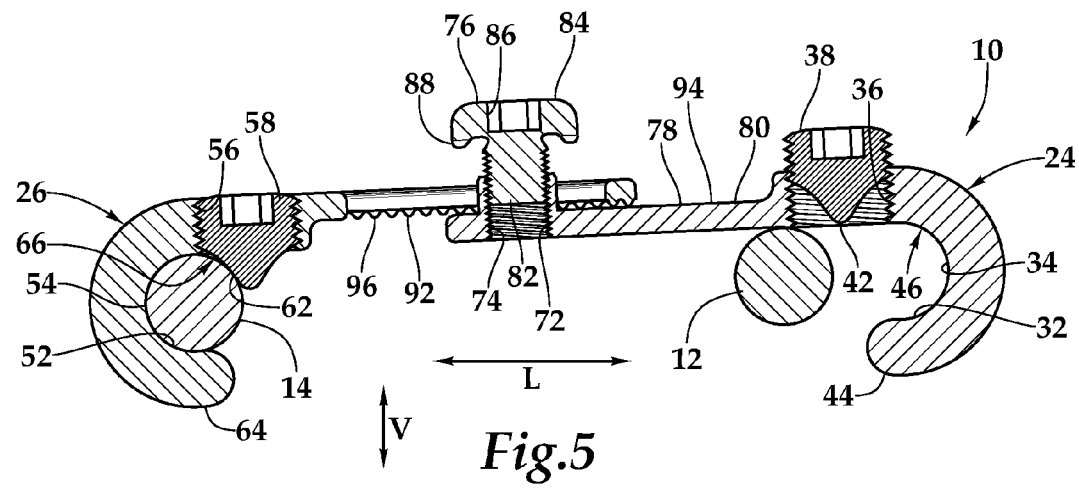
FIG. 5 is a side-cross sectional view of the spinal cross-connector of FIG. 1 in an operational embodiment being secured to rods.
Figure 6:
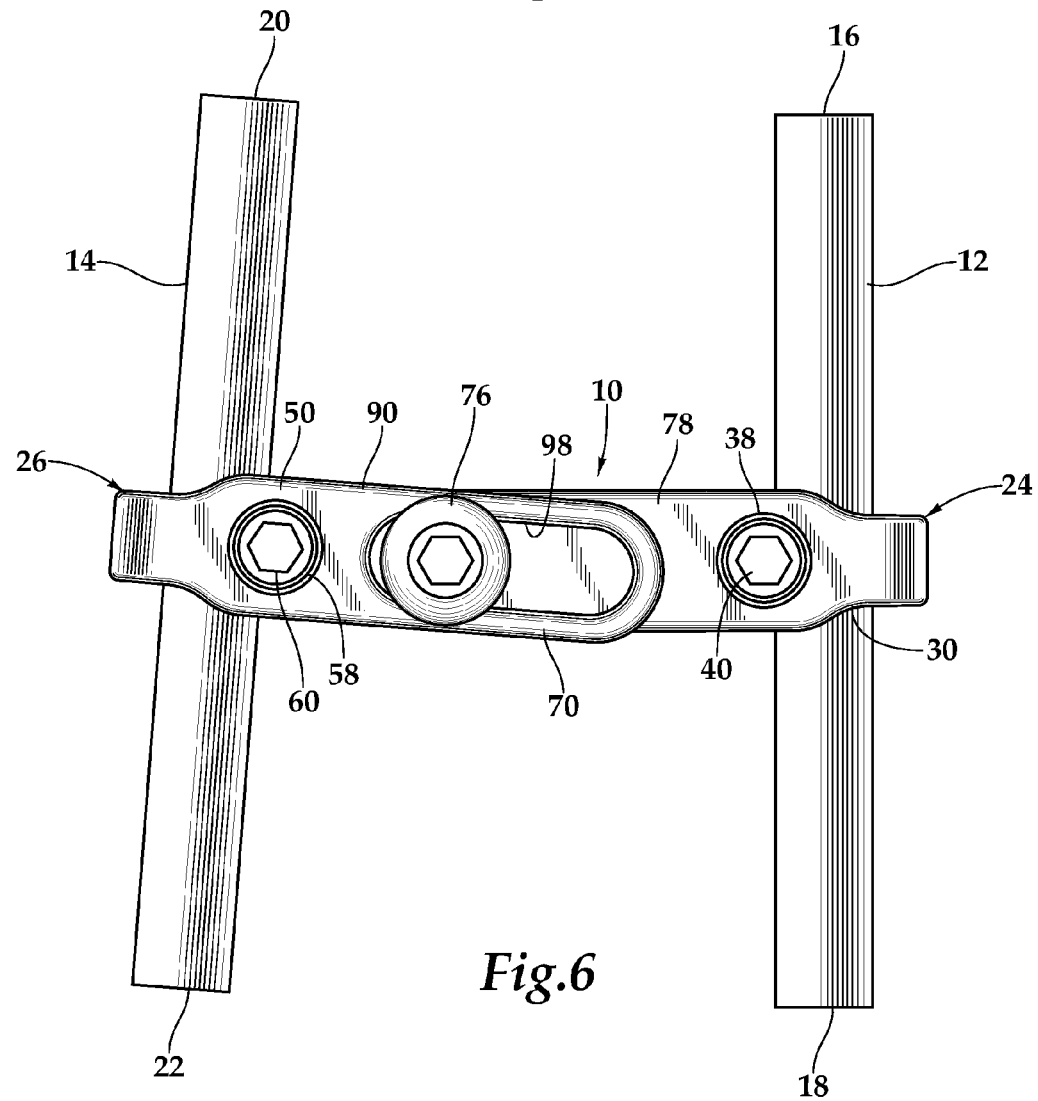
FIG. 6 is a top plan view of the spinal cross-connector in an operational embodiment being secured to rods.

Referring to FIG. 5 and FIG. 6, in operation, the spinal cross-connector 10 can compensate for skewed rods having a vertical displacement, V. In addition to being angle adjustable, the spinal cross-connector 10 is length, L, adjustable, thereby affording the spinal cross-connector 10 in situ sizing and adjustability. Rotational adjustment is provided through placement of the c-shaped arms 28 and 48 which may accommodate a wide range an angles relative to the respective rods 12, 14. In skewed applications requiring angular compensation, the set screws 38, 58 ensure that the rods 12, 14 are secured within the rod receiving spaces 46, 66. Length adjustment is achieved through proximate medial adjustment of the flat bar 70 of the coupling member 24 and the rack 90 of the coupling member 70 relative to each other by extending or retracting the linear alignment and overlap of the flat bar 70 and the rack 90.

More particularly, in implantation, the rack 90 is superposed onto the flat bar 70 such that the teeth 92 of the rack 90 frictionally engage the bearing surface 78 of the flat bar 70. The relationship and positioning of the rack 90 may be slidably adjusted along the length of the flat bar 70 such that there is a span of sufficient distance to permit each of the opposing coupling members 24, 26 to receive the respective orthopedic rods 10, 12. This span and the relative positioning of the rack 90 and the flat bar 70 may be fixed by tightening the threaded bolt 76. As the threaded bolt 76 is driven through the threaded lug 74, the teeth 92 are pressed down against the bearing surface 78 and the bearing surface 78 is raised into the teeth 92 such that the teeth 92 seize against the bearing surface 78 in compression contact or pressing contact. Structurally, in one embodiment, the selectively adjustable overlapping mechanical engagement between the rack 90 and the flat bar 70 is being provided by a fastener (e.g., threaded lug 74 and threaded bolt 76) which extends through the rack 90 and the bearing surface 78 of the flat bar 70. Additionally, in this one embodiment, the aperture 72 in the flat bar 70 is located not at the edge of the flat bar 70, but proximate thereto such that the flat bar may aid in providing compression contact on each side of the aperture 72 and fastener. In instances where the orthopedic rods 10, 12 are not exactly parallel, the displacement may be compensated for by the rack 90 and the biting of the teeth 92 onto the bearing surface 78 of the flat bar 70.

In another embodiment, the rack 90 and flat bar 70 have a moveable link and slot arrangement that provides for the threaded bolt 76 to be locked therein. In a further embodiment, the rack 90 and/or flat bar 70 may have a textured surface or contact profile formed from a corundum blast technique, for example. Alternatively still, the rack 90 and/or flat bar 70 may include teeth or a diamond pattern that provides a gripping surface.

In operation, the set screw 38, by the application of torque, is driven through the threaded bore 36 toward the orthopedic rod 12 until the lower end of the set screw 38 engages the orthopedic rod 12. As the set screw 38 continues to advance through the internal threads of the bore 36, the orthopedic rod 10 is urged into pressing contact with the gripping pocket 32 to secure the orthopedic rod 10 therein.

Similarly, set screw 58 may be selectively advanced through the threaded bore 56 into engagement with the rod 12. More particularly, in one embodiment, the set screw 58 includes a conical profile 62 extending substantially perpendicularly to the arcuate extension 64. The curved profile 62 of the set screw 58 enhances the gripping pocket 52 and continues the curvature therein to define a de-segmented circular curve or substantially circular curve extending along the gripping pocket 52 and the conical profile 62. The de-segmented segment of the de-segmented circular curve or incomplete circle or closed loop, which defines an open loop, is located along the surface of the rod 14, thereby exposing a portion of the rod.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A spinal cross-connector for connection between adjacent first and second rods, the spinal cross-connector comprising:
   a first coupling member including a bar extending from a first body portion opposite to and in longitudinal axial alignment with a first c-shaped arm, the bar including a flat bar;
   a bearing surface extending the length of the bar from a location proximate to the aperture to an end thereof;
   a second coupling member including a rack extending from a second body portion opposite to and in longitudinal axial alignment with a second c-shaped arm;
   the rack being superposed in a selectively adjustable overlapping mechanical engagement with the bearing surface, the rack including teeth that bite the bearing surface of the bar, the rack including a slot for receiving a threaded bolt which extends through the rack and into a threaded lug positioned in the bearing surface, the threaded bolt and threaded lug provide a compression contact between the rack and the bearing surface of the bar;
   the first c-shaped arm including an arcuate extension extending substantially parallel to the bar to define a gripping pocket; and
   a set screw selectively advanceable through the first body portion, the advance of the set screw operable to urge the first rod into pressing contact with the gripping pocket to secure the rod therein.

2. The spinal cross-connector as recited in claim 1, wherein the second c-shaped arm includes an arcuate extension extending substantially parallel to the bar to define a gripping pocket.

3. The spinal cross-connector as recited in claim 2, wherein another set screw is selectively advanceable through the second body portion to urge the second rod into pressing contact with the gripping pocket.

4. A spinal cross-connector for connection between adjacent first and second rods, the spinal cross-connector comprising:
   a first coupling member including a bar extending from a first body portion opposite to and in longitudinal axial alignment with a first c-shaped arm, the bar including a flat bar;
   a bearing surface extending the length of the bar from a location proximate to the aperture to an end thereof;
   a second coupling member including a rack extending from a second body portion opposite to and in longitudinal axial alignment with a second c-shaped arm, the rack including teeth that bite the bearing surface of the bar, the rack including a slot for receiving a threaded bolt which extends through the rack and into a threaded lug positioned in the bearing surface, the threaded bolt and threaded lug provide a compression contact between the rack and the bearing surface of the bar;
   the rack being superposed in a selectively adjustable overlapping mechanical engagement with the bearing surface;
   the first c-shaped arm including an arcuate extension extending substantially parallel to the bar to define a gripping pocket; and
   a set screw selectively advanceable through the first body portion.

* * * * *